(12) United States Patent
Felzmann

(10) Patent No.: US 7,867,488 B2
(45) Date of Patent: Jan. 11, 2011

(54) USE OF DENDRITIC CELLS (DCS) EXPRESSING INTERLEUKIN 12 (IL-12)

(75) Inventor: Thomas Felzmann, Ollern (AT)

(73) Assignee: Forschungsinstitut fur Krebskranke Kinder, Vienna (AT)

( * ) Notice: Subject to any disclaimer, the term of this patent is extended or adjusted under 35 U.S.C. 154(b) by 0 days.

(21) Appl. No.: 10/527,679

(22) PCT Filed: Aug. 29, 2003

(86) PCT No.: PCT/EP03/09591

§ 371 (c)(1),
(2), (4) Date: Mar. 11, 2005

(87) PCT Pub. No.: WO2004/024900

PCT Pub. Date: Mar. 25, 2004

(65) Prior Publication Data

US 2006/0177420 A1 Aug. 10, 2006

(30) Foreign Application Priority Data

Sep. 13, 2002 (AT) .............................. A 1375/2002

(51) Int. Cl.
*C12N 15/85* (2006.01)
*C12N 5/00* (2006.01)
*A61K 38/19* (2006.01)

(52) U.S. Cl. ..................... 424/93.7; 435/325; 435/372; 435/372.3; 435/375; 435/377; 424/85.1

(58) Field of Classification Search ................... None
See application file for complete search history.

(56) References Cited

U.S. PATENT DOCUMENTS 6,479,254 B2 * 11/2002 Ebner et al. ................. 435/69.1
2005/0059151 A1 * 3/2005 Bosch ........................ 435/372

OTHER PUBLICATIONS

Felzmann et al., Cancer Letters, Jul. 26, 2001, vol. 168:145-154.*
Asavaroengchai et al., PNAS, Jan. 22, 2002, vol. 99:931-936.*
Rieser, Urol. Int., 1999, vol. 63(3):151-159.*
Felzmann et al., Cancer Letters, 2000, vol. 161:241-250.*
Fong et al., Annu. Rev. Immunol., 2000, 18:245-273.*
Lopointe et al., Eur. J. Immunol., 2000, 30:3291-3298.*
Felzmann, Thomas et al., "Functional maturation of dendritic cells by exposure to CD40L transgenic tumor cells, fibroblasts or keratinocytes" Cancer Letters, vol. 168, No. 2, Jul. 26, 2001, pp. 145-154.
Rieser, Claudia et al., "Mature dendritic cells induce T-helper type-1-dominant immune responses in patients with metastic renal cell carcinoma" Urolgia Internationalis, vol. 63, No. 3, 1999, pp. 151-159.
Felzmann, Thomas et al., "Xenogenization by tetanus toxoid loading into lymphoblastoid cell lines and primary human tumor cells mediated by polycation and liposomes" Cancer Letters, Nol. 161, No. 2, Dec. 2000, pp. 241-250.

Cella, M. et al., "Ligation of CD40 on dendritic cells triggers production of high levels of interleukin-12 and enhances T-cell stimulatory capacity: T-T help via APC activation", Journal of Experimental Medicine, vol. 184, No. 2, 1996, pp. 747-752.
Banchereau, J. et al., "Dendritic cells and the control of immunity" Nature, vol. 392, Vo. 6673, Mar. 19, 1998, pp. 245-252.
Gitlitz, B.J. et al., "Dendritic cell-based immunotherapy of renal cell carcinoma", Current Urology Reports, vol. 2, No. 1, Feb. 2001, pp. 46-52.
Czerniecki, Brian J. et al., "Targeting HER-2/neu in early breast cancer development using dendritic cells with staged interleukin-12 burst secretion", Cancer Res., Feb. 15, 2007, vol. 67, No. 4, pp. 1842-1852.
Davis, Daniel M., "Mechanisms and functions for the duration of intercellular contacts made by lymphocytes", Nature Reviews Immunology, Aug. 2009, vol. 9, pp. 543-555.
Dohnal, A. M. et al., "Phase I study of tumor Ag-loaded IL-12 secreting semi-mature DC for the treatment of pediatric cancer", Cytotherapy, 2007, vol. 9, No. 8, pp. 755-770.
Dohnal, A. M. et al., "Comparative evaluation of techniques for the manufacturing of dendritic cell-based cancer vaccines", J. Cell. Mol. Med., 2009, vol. 13, No. 1, pp. 125-135.
Dohnal, A. M. et al., " CD40 ligation restores type 1 polarizing capacity in TLR4-activated dendritic cells that have ceased interleukin-12 expression", J. Cell. Mol. Med., 2009, vol. 13. No. 8, pp. 1741-1750.
Felzmann, Thomas et al., "Semi-mature IL-12 secreting dendritic cells present exogenous antigen to trigger cytolytic immune responses", Cancer Immunol. Immunother., 2005, vol. 54, pp. 769-780.
Huettner, Katharaina Gabriela et al., "Generation of potent antitumor immunity in mice by interleukin-12 secreting dendritic cells", Cancer Immunol Immunother, 2005, Vo. 54, pp. 67-77.
Kalinski, Pawel et al., "Final maturation of dendritic cells is associated with impaired responsiveness to IFN-γ and to bacterial IL-12 inducers: Decreased ability of mature dendritic cells to produce IL-12 during the interaction with Th cells", The Journal of Immunology, 1999, vol. 162, pp. 3231-3236.
Langenkamp, Anja et al., "Kinetics of dendritic cell activation: impact on primin of $T_H1$, $T_H2$ and nonpolarized T cells", Nature Immunology, Oct. 2000, vol. 1, No. 4, pp. 311-316.
Luo, Jun-Li et al., "IKK/NF-κB signaling: balancing life and death—a new approach to cancer therapy", The Journal of Clinical Investigation, Oct. 2005, vol. 115, No. 10, pp. 2625-2632.
Steinman, Ralph M. et al., "Taking dendritic cells into medicine", Nature, Sep. 27, 2007, vol. 449, pp. 419-426.
Suffredini, Anthony F. et al., "Dose-related inflammatory effects of intravenous endotoxin in humans: Evaluation of a new clinical lot of *Escherichia coli* O:113 endotoxi", The Journal of Infectious Diseases, 1999, vol. 179, pp. 1278-1282.

* cited by examiner

*Primary Examiner*—Elizabeth C. Kemmerer
*Assistant Examiner*—Xiaozhen Xie
(74) *Attorney, Agent, or Firm*—Birch, Stewart, Kolasch & Birch, LLP

(57) ABSTRACT

The present invention discloses the use of active dendritic cells (DCs) releasing interleukin 12 (IL-12) which are loaded with an antigen against a specific pathogen or a specific tumor and, due to the treatment with lipopolysaccharide (LPS) and interferon-gamma (IFN-γ), release IL-12, for the preparation of a medicament for treating a patient having an infection with said specific pathogen or for treating a patient having said specific tumor.

14 Claims, 9 Drawing Sheets

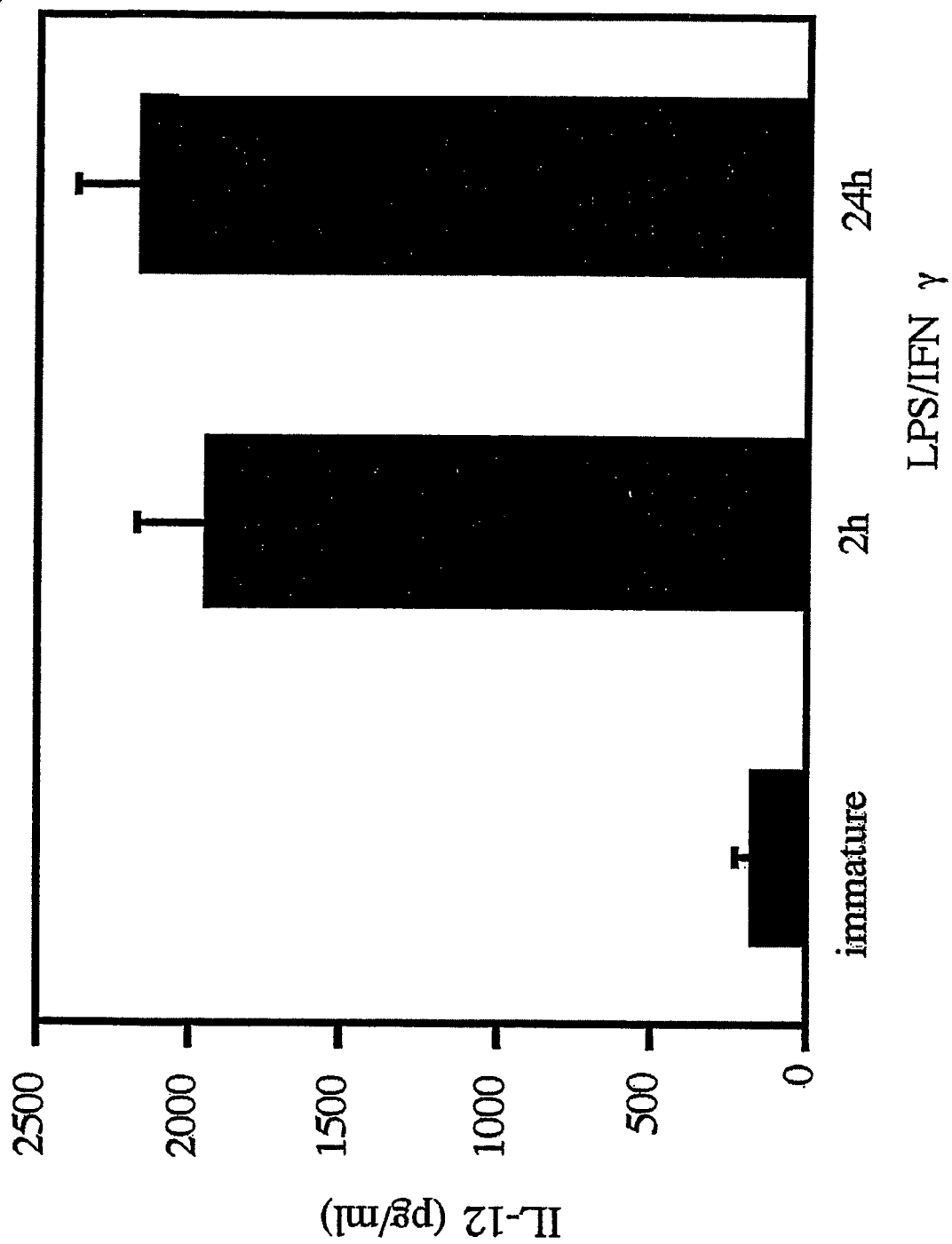

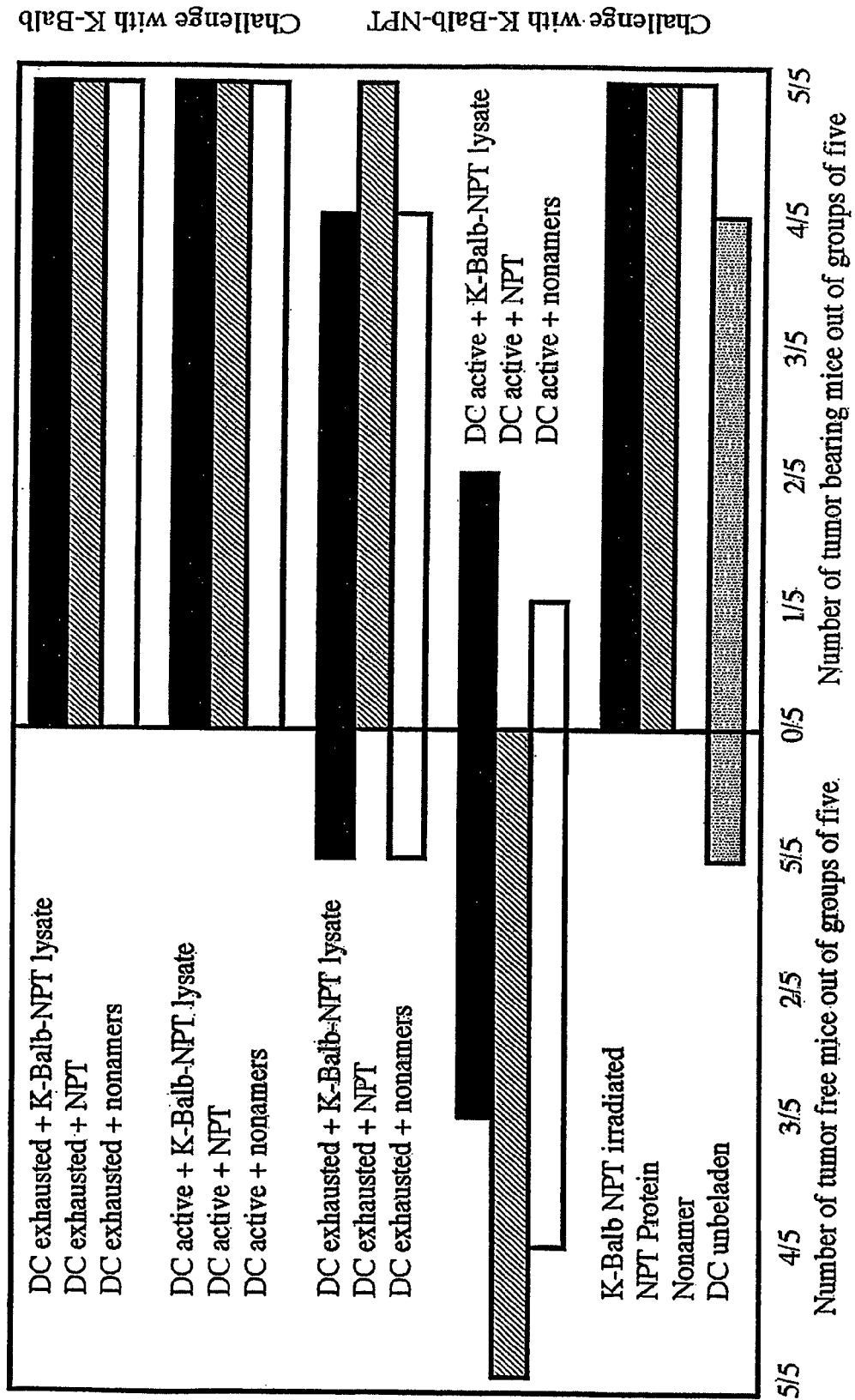

USE OF DENDRITIC CELLS (DCS) EXPRESSING INTERLEUKIN 12 (IL-12)

Figure 1:
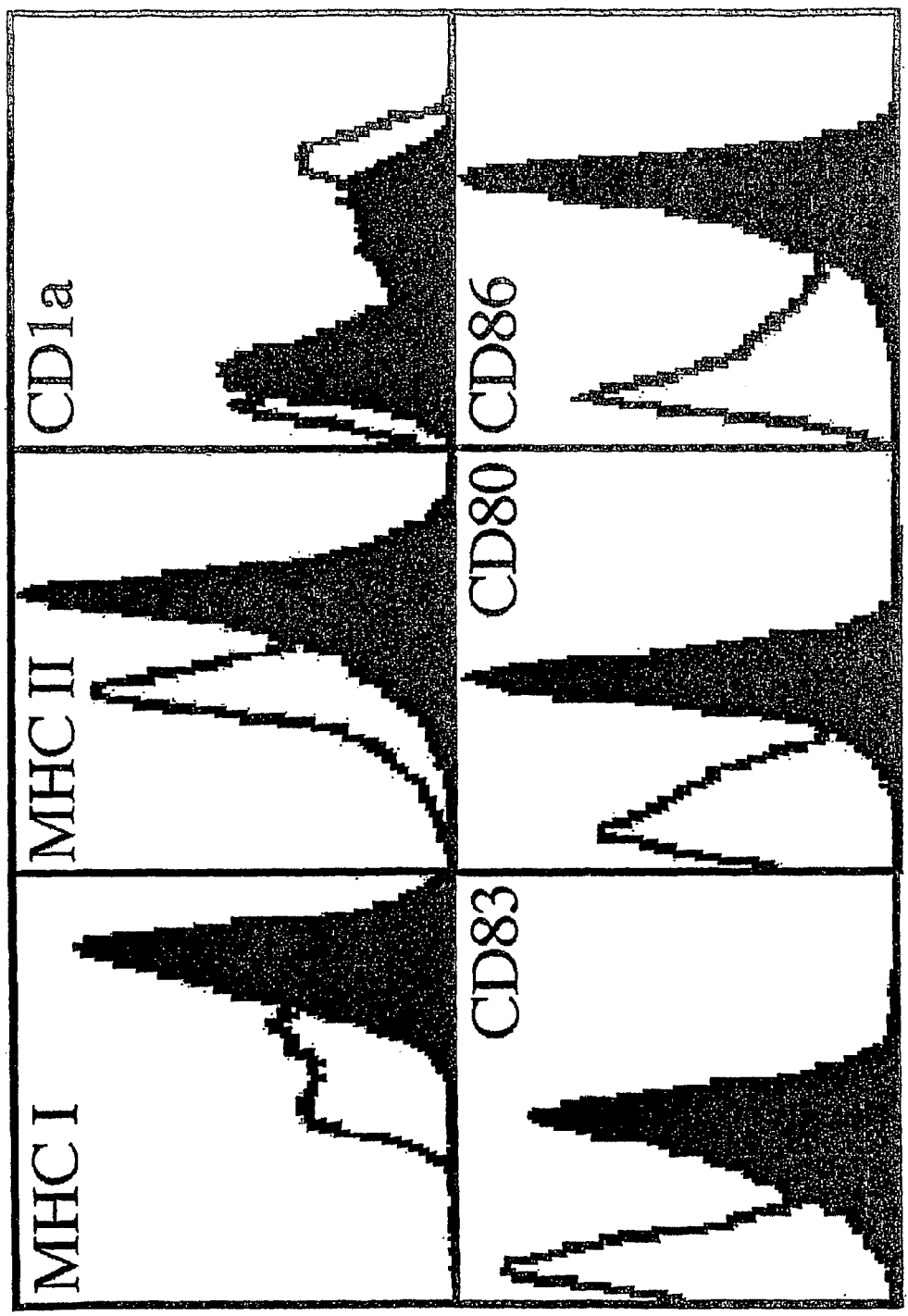

The invention relates to the use of dendritic cells (DCs) expressing Interleukin 12 (IL-12).

While there has been considerable progress in the development of techniques to identify tumor associated antigens, the traditional methods for delivering these antigens are, in many cases, crude and inadequate. Most adjuvants that are in principle available have been discovered empirically and their mechanism of immune stimulatory action is poorly understood. In addition, pre-clinical studies suggested that most conventional adjuvants support the generation of some kind of immune responses but fail to elicit other important arms of the immune system such as CTL activity. In particular, the generation of cytolytic anti-tumor immunity could not be accomplished by such adjuvants.

This led to the application of DCs as adjuvants. In such experiments DCs pulsed in vitro with tumor associated antigen caused tumor rejection in experimental mouse tumor systems and increased anti-tumor immunity in patients. DCs capture and process antigens in the periphery, migrate to lymphoid organs, express lymphocyte co-stimulatory molecules, and secrete cytokines to initiate and guide immune responses.

Antigen is presented by DCs on MHC class I and class II molecules, which bind peptides during their biosynthetic maturation thus providing a continuously updated display of the intracellular and environmental protein composition. T-cell receptors on cytotoxic T-lymphocytes (CTL) recognize antigenic peptides bound to MHC class I molecules, while MHC class II-peptide complexes are being recognized by helper T-lymphocytes (HTL).

Some maturation stimuli lead to type 1 HTL polarization characterized by IL-12 release [Cella, 1996] that subsequently supports the development of cytolytic immunity. Others fail to do so and favor type 2 HTL polarization that supports humoral immunity. Lipopolysaccharide (LPS) is a classical maturation stimulus that results in IL-12 secretion from DCs [Hilkens, 1997].

However, it was shown [Langenkamp, 2000] that after maturation with LPS DCs produced IL-12 only transiently and became refractory to further stimulation. The exhaustion of cytokine production impacted the T-lymphocyte polarizing process. Soon after stimulation DCs primed strong type 1 HTL responses, whereas at later time points the same cells preferentially primed type 2 HTLs.

In WO 01/39600 A1, the use of Hsp27 as anti-inflammatory agent has been described which is used for the maturing of DCs. These DCs, however, are not loaded with a tumor antigen, much rather the antigen contact occurs only after maturing has occurred. An antigen loading prior to maturing accordingly cannot occur in this document.

In WO 01/09288 A1, DCs i.a. are prepared by the addition of TNF-alpha in the culturing medium. However, it has been known that TNF-alpha does not stimulate the complete heterodimeric IL-12 molecule, but merely one of the two subunits. Furthermore, according to WO 01/09288 A1, the antigen contact becomes effective only after the DCs have matured, so that the cells described there in any case are not loaded against a specific pathogen or a specific tumor.

In WO 02/34887 A2, two different classes of nucleic acid adjuvants, i.e. CpGs on the one hand, and Poly-I:Cs on the other hand, are used for stimulating DCs. However, it has been known that Poly-I:C and CpG can release IL-12 in human DCs with very low efficiency only. Moreover, according to this document, a pathogen- or tumor-specific "loading" of the DCs in combination with the release of IL-12 is not described.

In WO 01/51077 A1, methods for regulating the IL-12 production by CCR5 agonists and antagonists are described, yet also there it is started out with specifically "loaded" DCs.

Wang et al. (Zhonghua xue ye xue za zhi, 21(7), (2000), pp. 345-348) describe that the proliferation of CD(4)(+) cells after cultivation with DCs should be a good indicator as an instrument for checking the progress of an immune therapy. DCs of PBMCs were loaded with a tumor antigen of the XG-7 cell line, which then could stimulate more CD(4)(+) cells than DCs. However, this document does not describe the administration of a maturation stimulus.

It is therefore an object of the present invention to provide improved means for treating viral infections and tumors using DCs.

The present invention therefore provides the use of dendritic cells (DCs) releasing interleukin 12 (IL-12) which are loaded with an antigen against a specific pathogen or a specific tumor and, due to the treatment with lipopolysaccharide (LPS) and interferon-gamma (IRN-γ), release IL-12, for the preparation of a medicament for treating a patient having an infection with said specific pathogen or for treating a patient having said specific tumor.

Although it was known that it is possible to induce IL-12 release in DCs, this concept has not been regarded as being suitable and necessary for treating tumor patients or for treating patients which have severe viral infections. This was mainly due to the fact that the IL-12 release of DCs is transient and therefore suitable for inducing a sufficient cellular immune response against the tumor or the pathogen only during a limited time window. Surprisingly, it could be shown with the present invention that the application of this concept to trigger the secretion of large amounts of IL-12 from DCs e.g. by exposure to a combination of LPS and IFN-γ under fetal calf serum free culture conditions resulted in a stabilisation of the disease for a prolonged period of time without any major toxic side effects. It is, however, important to deliver the DCs according to the present invention in a state, where IL-12 release still takes place, i.e. immediately after the preparation of the tumor- or pathogen-specific IL-12 releasing DCs or at least within 1 to 10, especially within 2 to 6 hours thereafter, ideally about 2 hours after completion of the preparation. The present invention therefore also relates to a method for administration of the DCs according to the present invention in an effective amount to a tumor patient or a patient being infected with the specific pathogen.

Indeed, the treatment provided with the present invention is well tolerated. It could therefore be shown by the present invention that such active DCs, in contrast to exhausted DCs that do not produce IL-12 any more, were able to induce cytolytic immunity in a human in vitro model and tumor rejection in a mouse tumor model. First preliminary results of a clinical phase I of the present invention are reported in the example section of the present application which show the feasibility and lack of toxicity of an IL-12 secreting DC-ATIT (anti-tumor immune therapy) immune therapeutic for the treatment of cancer.

Another method to trigger IL-12 release from DCs is the delivery of a signal mediated by the interaction of the CD40 molecules on the surface of DCs with its ligand CD40L. The combination of LPS and IFN-γ shows the best IL-12 stimulation in the present therapeutic setting for the phase I trial according to the present invention.

The use or method according to the present invention is also preferred for patients which have suffered a bone marrow transplantation which are suffering from a viral infection that is caused by immune deficiency in the course of bone marrow transplantation before the treatment with the DCs according to the present invention.

The present invention may be used for a wide range of pathogens or tumors. Preferably, the specific tumor to be treated with the DCs according to the present invention is a solid advanced malignancy. In principle, any tumor at any stage may be the target of a cytolytic immune response that is induced with DCs according to the present invention.

The present invention is preferably performed using autologous DCs. Therefore, it is preferred to use DCs or precursor cells of DCs having been taken from the patient having an infection with said specific pathogen or from the patient having said specific tumor or in the context of a bone marrow transplantation from the bone marrow donor. These autologous DCs are connected with the lowest adverse reactions, because they are recognised as "self" by the patient's immune system.

Loading of the DCs may be carried out with any antigen or antigen mixture being specific for the tumor or pathogen, e.g. with isolated or chemically or recombinantly produced polypeptides. Preferably, however, the DCs are loaded with an antigen from a tumor cell lysate from said patient having said specific tumor. Such autologous tumor preparations show significant successes in clinical trials according to the present invention.

For appropriate tracking and controlling of the administration of the DCs and the immunological response of the patient thereto, it is preferred to charge the DCs additionally with a tracer antigen, especially with keyhole limpet hemocyanine (KLH). In principle, each neoantigen, that is an antigen that was never before encountered by the human immune system, is suitable as a tracer antigen.

In order to further enhance the immune response for the present invention it may be preferred to additionally charge the DCs with an adjuvant, especially with tetanus toxoid. In principle, each recall antigen, that is an antigen against a strong immune response may be expected because of previous routine vaccinations, is suitable as an adjuvant antigen.

The source of DCs is not critical. Since preparing DCs from peripheral blood mononuclear cells (PBMCs) is a standard technique, it is also preferred to generate the DCs to be used according to the present invention from peripheral blood mononuclear cells (PBMCs), especially PBMCs from the patient to whom the DCs should then be transferred after loading.

The cells activated according to the invention are DCs releasing interleukin 12 (IL-12) which are loaded with an antigen against a specific pathogen or a specific tumor.

The DCs activated according to the present invention may preferably be loaded with an antigen from a tumor cell. That antigen may be generated by lysis of tumor cells or tumor tissue, the tumor antigen may be generated in any recombinant expression system, or small peptides derived from the tumor antigen may be generated by chemical synthesis.

According to a preferred embodiment, the DCs activated according to the present invention are additionally charged with a tracer antigen.

The invention is further described by the following examples and the drawing figures, yet without being restricted thereto.

FIG. 1: Immune phenotye of immature and mature DCs. A typical immune phenotype of DCs before (open histograms) and after (closed histograms) exposure to an LPS/IFN-γ maturation stimulus is depicted.

Figure 2:
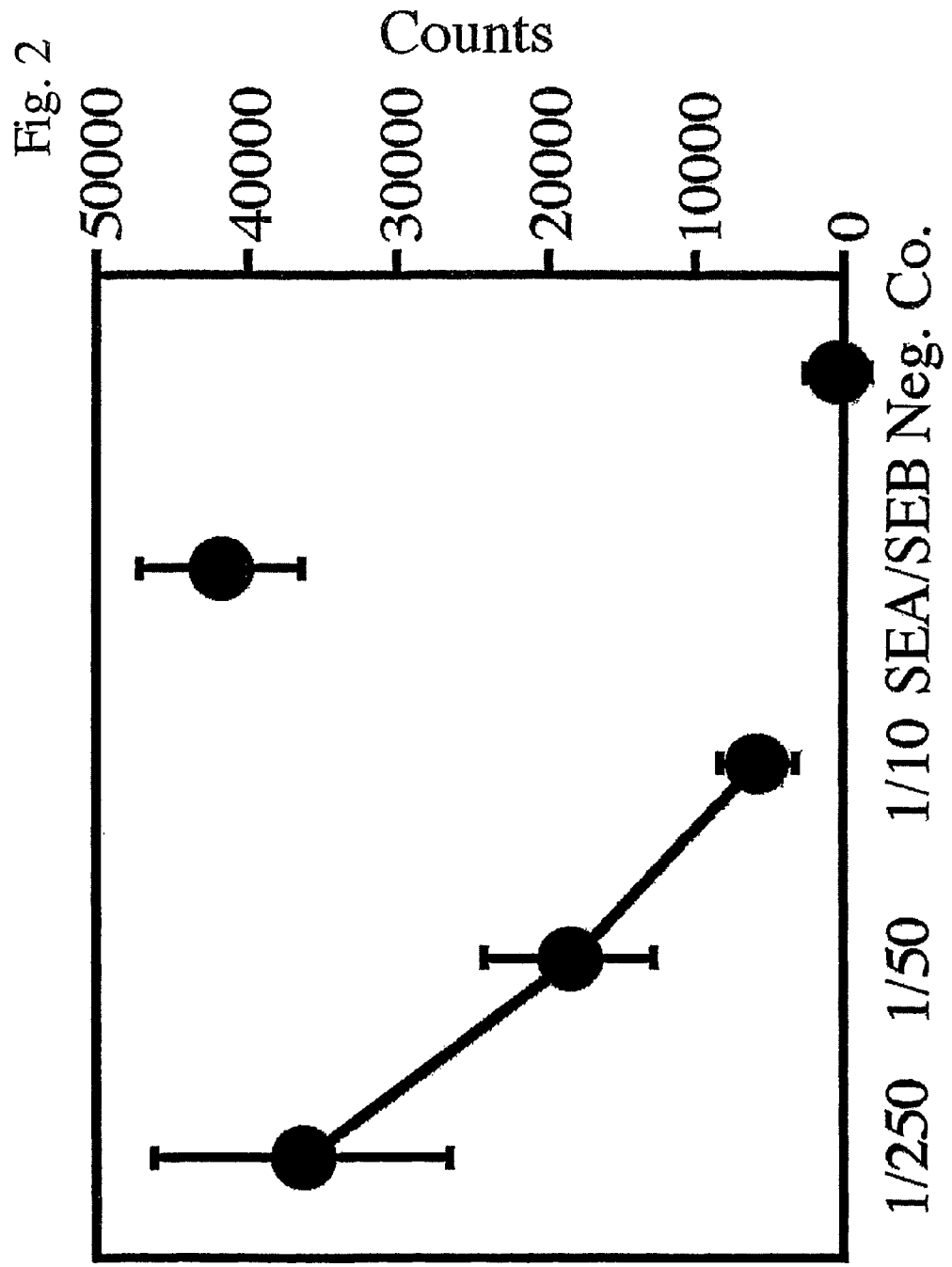

FIG. 2: Mixed leukocyte reaction. DCs were matured with LPS/IFN-γ and used to trigger proliferation in allogeneic lymphocytes. As positive control the superantigens SEA and SEB were used. The mean±SEM of 18 independent experiments is shown.

Figure 3:
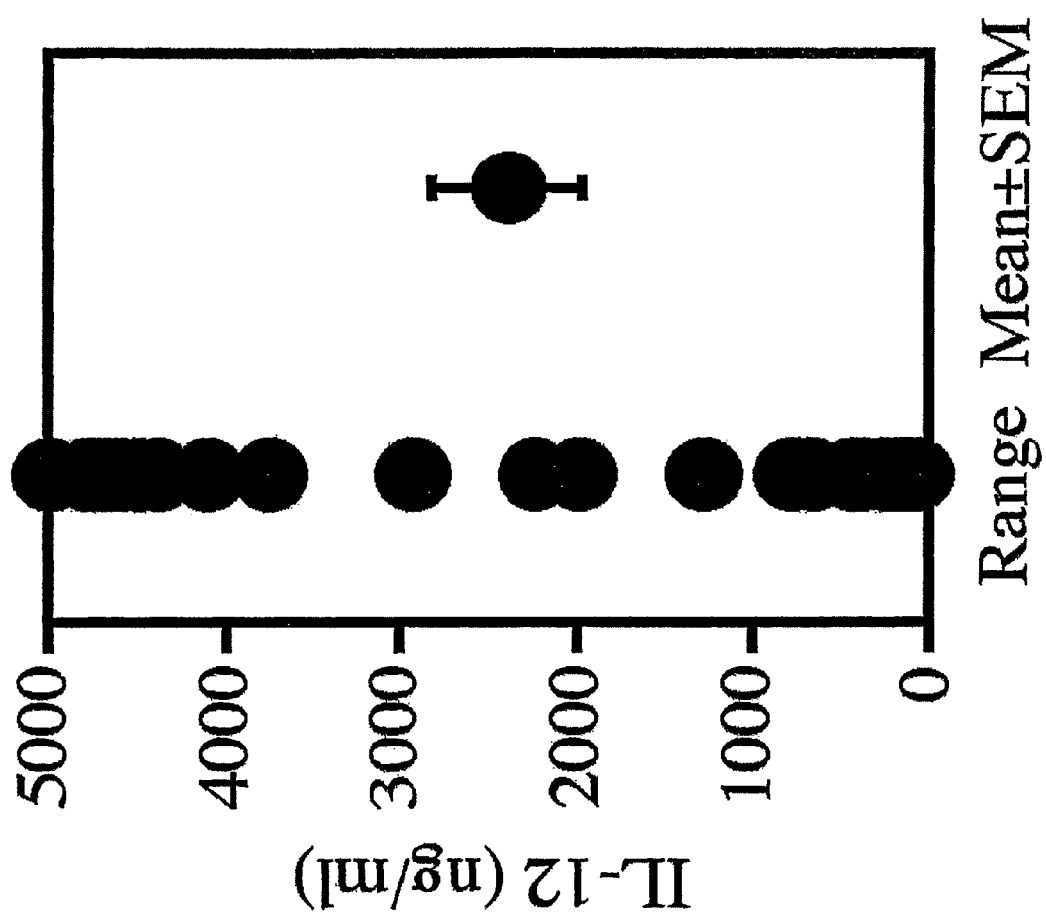

FIG. 3: IL-12 p70 heterodimer production by DCs. DC cultures were maturated with LPS/IFN-γ and the IL-12 secretion was determined after 24 hours. Individual data (left side) and mean±SEM (right side) from 23 independent experiments are shown FIG. 4: Antigen-specific expansion of autologous T-lymphocytes. Active (full circles, n=10) and exhausted (open circles, n=10) DCs loaded with autologous soluble lysate of LCLs were used for the antigen-specific expansion of T-lymphocytes. Shown is the absolute cell number as mean±SEM at the days of restimulation on a logarithmic scale.

Figure 5:
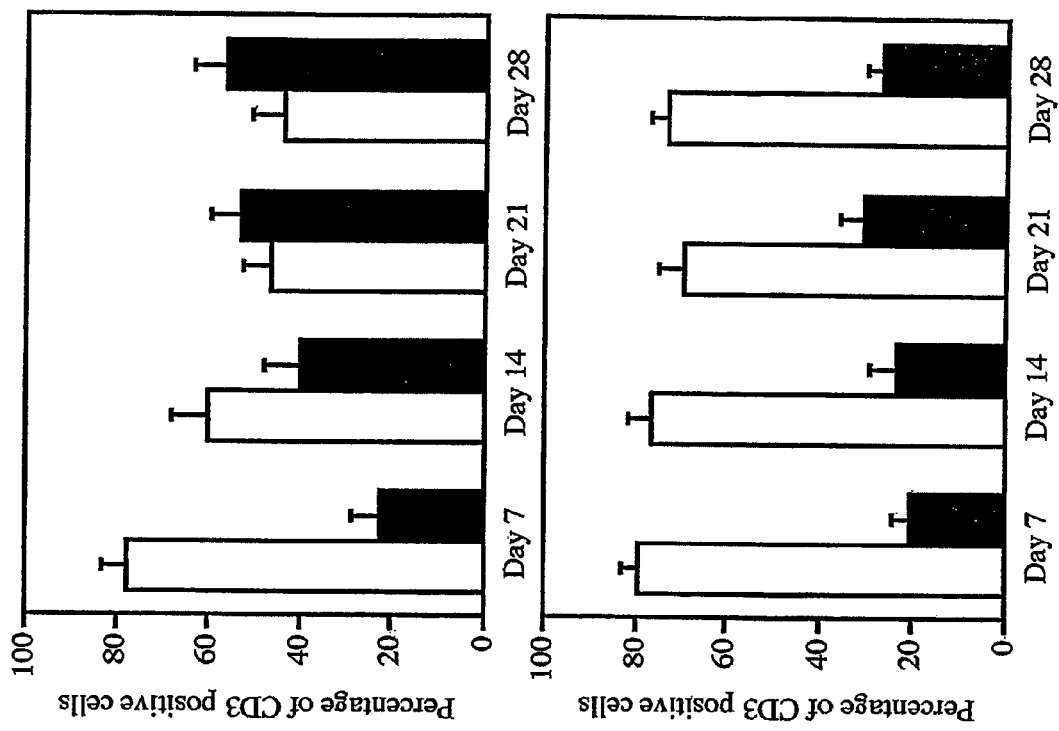

FIG. 5: Subset distribution of CD3-positive T-lymphocytes during antigen-specific expansion. Active DCs (upper panel, n=10) and exhausted DCs (lower panel, n=10) charged with autologous LCL-derived lysate were used to stimulate autologous T-lymphocytes weekly for four weeks. The subset distribution of CD3-positive T-lymphocytes was determined weekly by immune phenotyping (CD4-positive HTLs, full bars; CD8-positive CTLs, open bars). The percentage of the subpopulations is given as mean±SEM on the days of restimulation.

Figure 6:
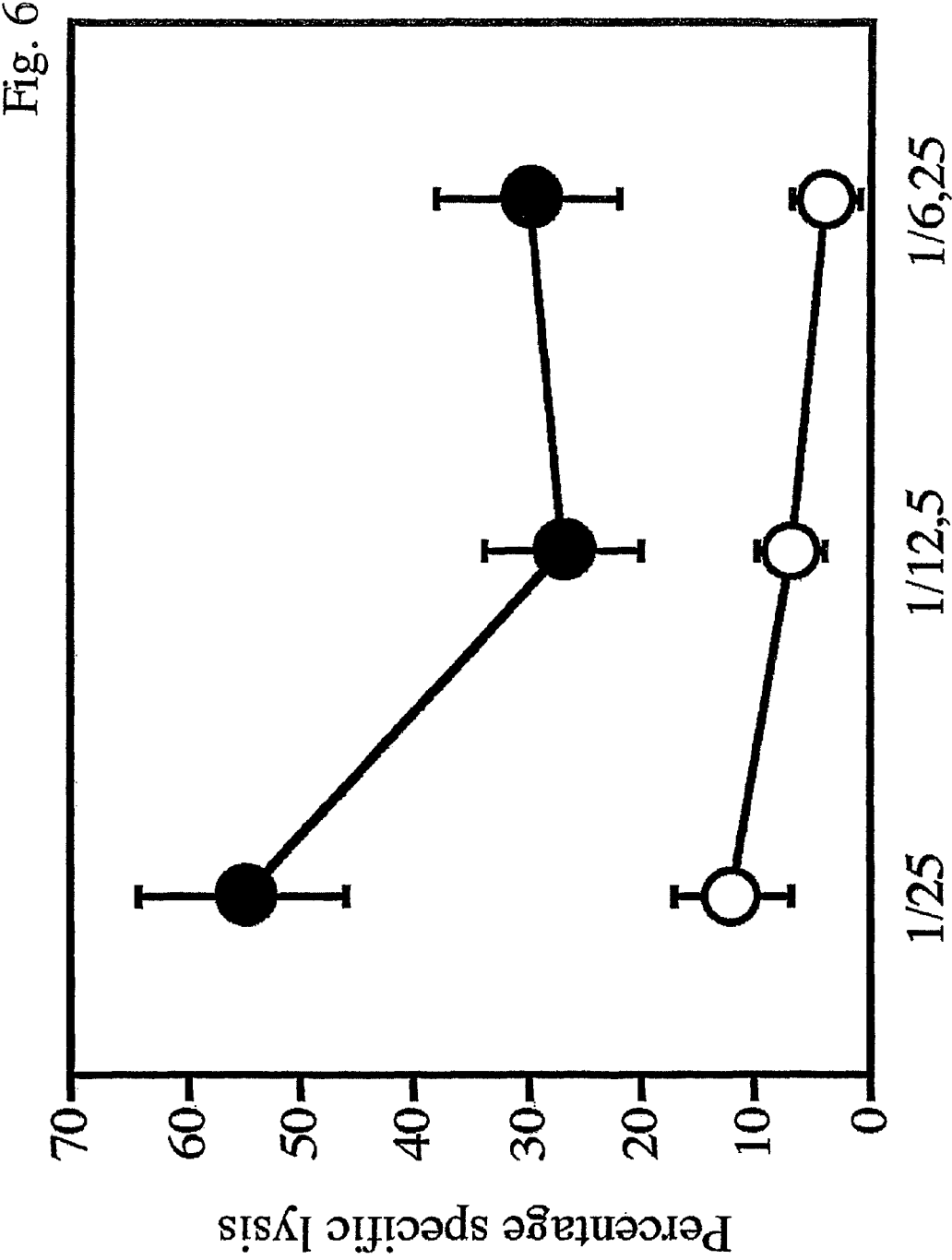

FIG. 6: Cytolytic activity of T-lymphocytes after antigen-specific expansion. Active DCs (full circles, n=3) and exhausted DCs (open circles, n=5) charged with autologous LCL-derived lysate were used to stimulate autologous T-lymphocytes weekly for four weeks. On day 28 the cytolytic activity of the expanded T-lymphocyte population was analyzed. Shown is the percentage of specific lysis as mean±SEM at the indicated effector/target ratios.

Figure 7:
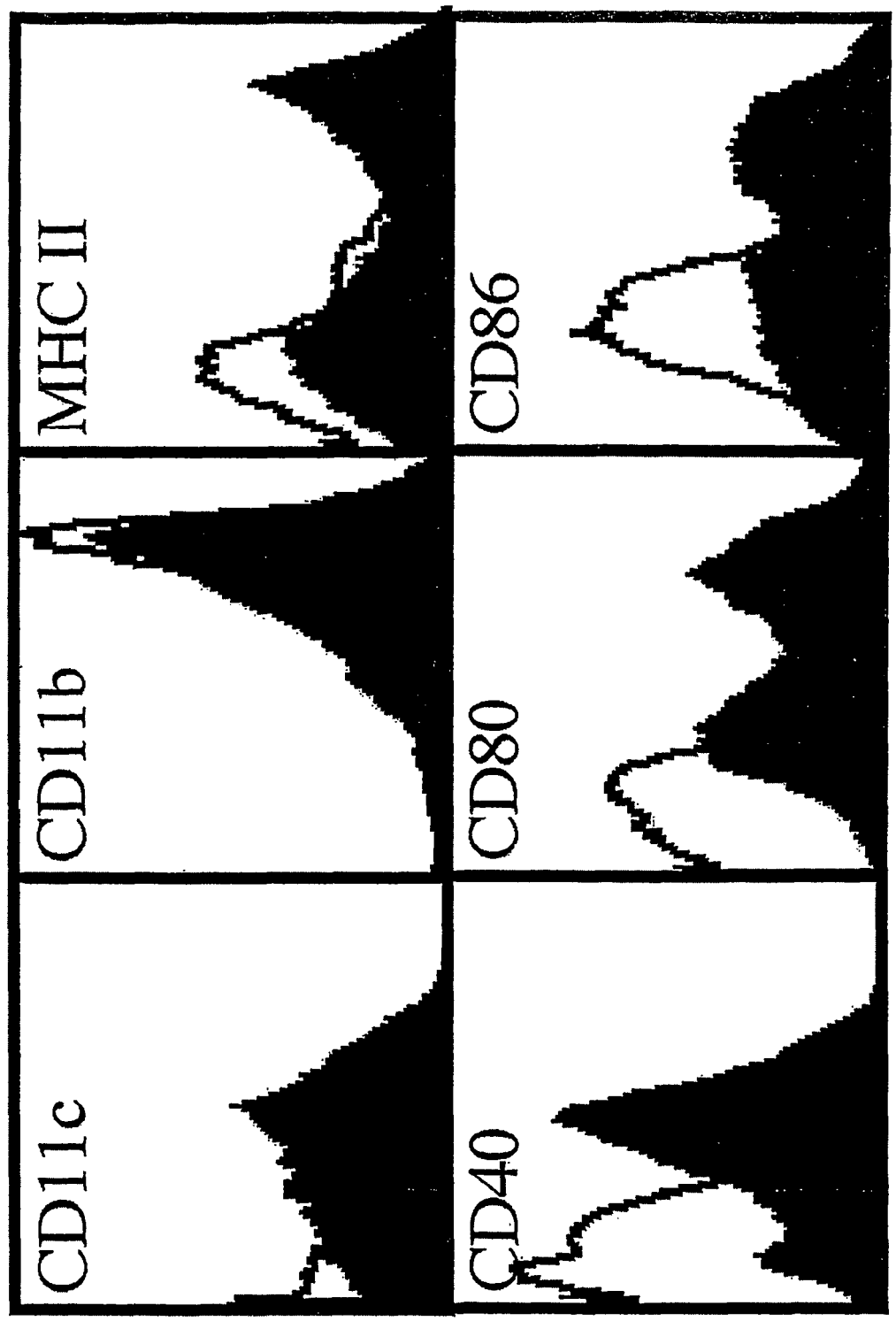

FIG. 7: Immune phenotye of immature and mature mouse DCs. A typical immune phenotype of DCs before (open histograms) and after (full histograms) exposure to a LPS/IFN-γ maturation stimulus is shown. Results of one representative experiment are depicted.

FIG. 8: Concentration of IL-12 p70 heterodimer in the culture supernatants after different LPS/IFN-γ stimulation periods. DCs were washed 2 hours after LPS/IFN-γ stimulation and re-cultured for 24 hours in DC cultivation medium or left for 24 hours in medium without removing LPS and IFN-γ. Data of three experiments are shown as mean±SEM.

FIG. 9: Protection of mice from a tumor expressing NPT as a model antigen. Groups of 5 mice were immunized as indicated with active or exhausted DCs, or control reagents. The DCs were charged with K-Balb-NPT lysate (full bar), recombinant NPT protein (hatched bars), or NPT-derived synthetic peptides (open bars). For the tumor challenge K-Balb wild type tumor cells and K-Balb-NPT tumor cells were used. The controls were challenged with K-Balb-NPT tumor cells. One representative experiment is depicted.

EXAMPLE

METHODS

Generation of Human Dendritic Cells

Peripheral blood mononuclear cells (PBMC) are collected by leukapharesis (Amicus, Baxter, Vienna, Austria). The leukapheresis product is diluted with PBS 1:5 and Ficoll-Hypaque (Amersham Pharmacia Biotech AB, Uppsala, Sweden) solution is layered underneath. The gradient is centrifuged 30 min at 2200 rpm, 180 to 20° C., without brake. The PBMC layer is transferred to another centrifuge tube and the cells are washed with excess PBS. The PBMCs are counted on a Sysmex F820 (Sysmex, Kobe, Japan) instrument and frozen in appropriate aliquots. For DC generation one aliquot of PBMCs is thawed and counted. One million DCs/ml are cultivated in AIM-V medium (Invitrogen Corporation, Bethesda, MD) with 1% pooled human AB plasma (Octaplas, Octapharm, Vienna, Austria) for two hours at 37° C. in a humidified incubator. Nonadherent cells are removed by carefully rinsing the plate. The adherent cells are cultivated for 5 days in AIM-V medium supplemented with 2% human plasma, 400 U/ml IL-4 (Pan Biotech GmbH, Aidenbach, Germany), and 1000 U/ml GM-CSF (Roche, Basel, Switzerland). On day 5 the cells are recovered, washed with PBS, and resuspended in AIM-V without plasma. One million DCs/ml are exposed to 1-10 µg of antigen for 2 h at 37° C. Without washing the DC culture is supplemented to a final concentration of 200 U/ml LPS (US Pharmacopeia, Rockville, Md.), 50 ng/ml IFN-γ (Boehringer Ingelheim, Vienna, Austria), 400 U/ml IL-4, 1000 U/ml GM-CSF, and human plasma to a final concentration of 2%. The cells are incubated for 2 hours at 37° C. for application as active IL-12 releasing DCs and for 48 hours for application as exhausted DCs. After completion of the maturation step the DCs are washed twice with PBS.

Generation of Mouse Dendritic Cells

In contrast to human DCs, murine-DCs are generated from bone marrow stem cells. Other than that the procedure is similar to the human system. Mouse bone marrow stem cells of Balb/c mice are collected from the long bones by cutting off the ends of the bones and flushing the shafts with a small syringe. The bone marrow cells are cultivated in RPMI medium (Invitrogen Corporation, Bethesda, Md.) with 10% fetal calf serum (PAA Laboratories, Linz, Austria) for 6 days in the presence of the 5 ng/ml murine IL-4 and 3 ng/ml murine GM-CSF (both purchased from Invitrogen Corporation, Bethesda, Md.) on a 24 well plate at a density of $10^6$ DCs/well. The loading with antigen is done in the same way as for human DCs (see above). For maturation LPS is used at a concentration of 100 ng/ml and murine IFN-γ (Invitrogen Corporation, Bethesda, Md.) is used at a concentration of 10 ng/ml. The animal safety committee of the University of Vienna Medical School approved all animal experiments.

Immune Phenotyping

The immune phenotype is analyzed before and after maturation according to standard procedures. IgG-Fc receptors are blocked by adding 50 µl 4% IgG solution to each test tube. For the analysis of human DCs the following MAB pairs are used: IgG FITC—IgG PE; CD45 FITC—CD14 PE; MHCII FITC—MHCI PE; CD1a FITC—CD83 PE; CD86 FITC—CD80 PE. For the analysis of mouse DCs the MABs CD11b PE, CD11c FITC, MHC II PE, CD80 PE, CD40 FITC, CD86 PE were used. MABs were purchased from DAKO, Glostrup, Denmark, Immunotech, Marseille, France, or Invitrogen Corporation, Bethesda, Md. Flow cytometry is done using a FACScan instrument (Becton Dickinson, San Jose, Calif.).

Mixed Leukocyte Reaction

PBMCs are isolated by gradient centrifugation from peripheral blood as described above and resuspended in AIM-V/2% human plasma. The DCs (10,000, 2,000, or 400) are placed in triplicates (100 µl per well) on a 96 well round bottom plate and $10^5$ allogeneic MNCs in 100 µl medium are added to each well. For a positive reference $10^5$ MNCs are stimulated in 100 µl medium with Staphylococcal enterotoxin A/B (SEA/SEB, Toxin Technologies Inc., Sarasota, Fla.) to 100 ng/ml final concentration. The mixed cells are incubated for 4 days. On day 4, 25 µl of tritium thymidine solution (NEN Life Science Products, Boston, Mass.) are added to each well and the cells are incubated for another 18 hours. Finally, the cells are harvested with a Skatron (Skatron, Lier, Norway) harvesting device and the incorporated tritium thymidine is counted on a Trilux beta-counter (Wallac Oy, Turku, Finland).

IL-12 ELISA

The appropriate number of wells is coated with IL-12 antibody (Invitrogen Corporation, Bethesda, Md.) in PBS and the plate is incubated over night at 4° C. On the next day the plate is washed, 250 µl of blocking solution (2%. bovine serum albumine in PBS) is added and the plate is incubated at room temperature for 3 hours. The plate is washed again and the samples and IL-12 standards (Invitrogen Corporation, Bethesda, Md.) are added at the appropriate dilution. Standard concentrations are 2500, 500, 100, 20, 4 pg/ml. The plate is incubated at room temperature over night. After another washing step 75 µl biotinylated IL-12 antibody solution (Invitrogen Corporation, Bethesda, Md.) is added, the plate is incubated at room temperature for 4 hours, washed again and 75 µl streptavidin-alkaline phosphatase (Chemicon, Temecula, Calif.) solution is added. After 1 hour incubation at room temperature, 100 µl PNPP (Sigma, St. Louis, Mo.) in diethanolamine buffer (48 ml 10 M diethanolamine, 0.25 ml 1 M $MgCl_2$, 20 ml 3 M HCl, adjusted to 500 ml water and pH=9.8) is added and the plate is incubated 50 minutes in the dark at room temperature. Finally, 50 µl 3 M NaOH is added to stop the reaction and the plate is measured with an ELISA plate reader (Anthos, Salzburg, Austria) at 405 nm using 690 nm as reference wavelength.

In Vitro Induction of a Cytolytic Immune Response

EBV transformed lymphoblastoid B cell lines (LCL) were generated by infection of B-lymphocytes with EBV produced by B95.8 cells. LCLs were grown in RPMI medium (Life Technologies, Grand Island, N.Y.) supplemented with 10% fetal calf serum (PAA Laboratories, Linz, Austria) and L-Glutamin. Continuously growing cultures were transferred to RPMI medium supplemented with 4% human plasma. Lysates of LCLs were prepared by five freeze thaw cycles in sterile water. Particulate components were removed from the protein solution by centrifugation. The protein concentration was determined using a Bio-Rad protein assay (Bio-Rad, Munich, Germany) according to the specifications of the manufacturer. Autologous lymphocytes were exposed at a previously optimized ratio of 5:1 to DCs charged with LCL-derived soluble protein. As negative control unloaded DCs were used. The cultures were kept in X-VIVO 15 medium (Bio-Whittaker, Watersville, Md.) supplemented with 1% human plasma, and 10 ng/ml IL-2 ("Proleukin", Chiron, Emeryville, USA) at a starting concentration of $1 \times 10^6$ lymphocytes/ml. The lymphocytes were re-stimulated every week for four weeks. The cell number was determined using a Coulter Z2 instrument (Coulter, Hialeah, Fla.). The lymphocyte subset distribution was analyzed by flow cytometry using monoclonal antibodies against CD3, CD4, and CD8 (all purchased from Invitrogen Corporation, Bethesda, Md.) according to standard procedures.

The cytolytic activity generated in the T-lymphocyte cultures was determined against fresh autologous and allogeneic target cells. LCLs were washed in medium and re-suspended in 1 ml buffer containing 80 µM $EuCl_3$ (Fluka, Buchs, Switzerland), 400 µM $DTPA-Na_2$, 250 µg/ml dextransulfate (MW 500,000), 50 mM Hepes (pH 7.4), 93 mM NaCl, 2 mM $MgCl_2$, and 5 mM KCl (all from Merck, Darmstadt, Germany) and incubated for no longer than 15 min at 4° C. on a turning wheel. Subsequently, 20 µl CaCl₂ were added and incubation continued for another 5 min and washed 3 times in a buffer containing 50 mM Hepes (pH 7.4), 93 mM NaCl, 2 MM MgCl₂, 5 mM KCl, 2 mM CaCl₂, and 10 mM glucose. The pellet was re-suspended in 20 ml medium and pre-incubated on a shaking platform in 75 cm² tissue culture flasks for 40 min at 37° C. Finally cells were washed again, re-suspended in medium and adjusted to 5×10⁴/ml. 100 µl of this cell suspension was transferred into the appropriate number of wells on a 96 well round bottom plate. Additional wells were set up for determination of spontaneous and maximum release (the latter by lysing the cells in 1% Triton X-100) of Eu from LCLs. The pre-stimulated T-lymphocytes were collected, washed once, and adjusted to an effector/target ratio of 25/1, 12.5/1, and 6.25/1 (final volume 200 µl). The plate was centrifuged at 500 rpm for 5 min without braking. After 4 hours incubation at 37° C. the plate was centrifuged again and 25 µl of the supernatants was transferred into a 96 well flat bottom plate and stored at 4° C. Before measurement, 200 µl enhancement solution was added, the plate was carefully shaked and the fluorescence was analyzed by time-resolved fluorimetry on a Wallac 1420 VICTOR multilabel counter (Wallac, Turku, Finland). Results were calculated as percentage specific lysis by the formula: % Lysis=(Experimental Counts−Spontaneous Release)×100/(Maximum Release−Spontaneous Release).

House Tumor Model

The mouse tumor cell line K-Balb that is syngeneic to Balb/c mice was used. This cell line was engineered to express neomycin phosphotransferase (NPT) by retroviral gene transfer. This xenogeneic protein served as an artificial tumor antigen in immunization experiments. Three antigen sources were used. First, recombinant NPT protein was generated in a commercially available bacterial expression system (Qiagen, Hilden, Germany) that has a histidine tag for protein purification according to the manufacturers recommendation. Second, the sequence of NPT was analyzed for nonameric peptides that have a high probability of binding to H2b molecules and being presented by DCs of Balb/c mice. For this analysis the "SYFPEITHI database of MHC ligands and peptide motifs" (http://syfpeithi.bmi-heidelberg.com) was used. The two peptides GYDWAQQTI and PVLFVK-TDL were found to have the highest binding probability. The third antigen source was whole tumor cell lysate obtained by five freeze thaw cycles with a subsequent centrifugation step to remove particulate components from the lysate. The protein concentration of these lysates was determined in the same way as the protein concentration of LCL-derived lysates (see above).

DCs were charged with 1 µg/ml synthetic NPT-derived peptides, recombinant NPT protein, or 10 µg/ml K-Balb-NPT lysate by incubation of the DCs for 2 hours in serum free medium. Subsequently, without prior washing serum was added to the cultures and the DCs received the LPS/IFN-γ maturation stimulus for 2 or 24 hours. After maturation DCs were washed twice in PBS and recovered in NaCl at a concentration of 10⁷ DCs/ml. One million antigen-charged and maturated DCs were injected subcutaneously on the back of shaved Balb/c mice in groups of five mice. Immunization was repeated after 1 week and after 2 more weeks the mice were challenged with 10⁶ K-Balb or K-Balb-NPT cells that were grown in fetal calf serum free medium for at least one week before injection. The tumor cells were injected subcutaneously on the oppostive flank of the mice and tumor growth was monitored.

Clinical Trial Design

Pediatric patients with solid tumors of childhood that have exhausted all conventional treatment options were recruited. Tumor tissue was obtained by surgery and mechanically disrupted to venerate a single cell suspension. The ratio of tumor and stroma cells was evaluated in a diagnostic laboratory by fluorescence in situ hybridization (FISH) according to standard procedures using informative markers for cytogenetic anomalies of the tumor cells. The single cell suspensions contained 50-90% tumor cells. The ethics committee of the St. Anna Children's Hospital, Vienna, Austria approved this clinical trial.

Peripheral blood mononuclear cells were collected from patients by leukapheresis and DCs generated as described above. The DCs were loaded with 10 µg/10⁶ DCs/ml autologous tumor cell lysates generated by five freeze-thaw cycles and removal of particulate components by centrifugation. The concentration of soluble protein was determined as described for LCL-derived lysates. In addition DCs were charged with keyhole limpet hemocyanine (KLH) that was used as a tracer antigen in delayed type hypersensitivity (DTH) testing and with tetanus toxoid (TT) as an adjuvant (both substances were purchased from Calbiochem, San Diego, Calif.). Subsequently the DCs received an LPS/IFN-γ maturation stimulus for 2 hours. The antigen loaded DCs were washed three times and mixed at a ratio of 1:1 with irradiated autologous tumor cells. DCs (1-10×10⁶/m²) were injected close to tumor free lymph nodes at weekly intervals for three weeks with a resting-period of three weeks after three injections. This procedure was repeated three times. Furthermore patients received treatment with IFN-γ to enhance the expression of MHC class I molecules thereby contributing to the prevention of escape from cytolytic immunity. IFN-γ was administered during the three weeks of tumor vaccine application by three subcutaneous injections per week at standard dosages.

A basic evaluation of clinical and laboratory parameters as well as disease monitoring were carried out before and after treatment by the appropriate methods. Other diagnosis was done as deemed clinically necessary. Side effects of the treatment were evaluated according to WHO standards. DTH testing against KLH and against irradiated tumor cells was used to assess the efficiency of the immunization procedure. Tumor cell lysate (1 µg in 100 µl NaCl), KLH (1 µg in 100 µl NaCl), 100 µl DC cultivation medium, or 100 µl NaCl were injected intradermally. The swelling and redness at the injection site was used as a measure for the induction of an immune response.

RESULTS

1. Analysis of Human Dendritic Cells 1.1. Immune Phenotype

Immature DCs were generated and subjected to an LPS/IFN-γ maturation stimulus. The immune phenotype was analyzed before and after maturation for up-regulation of the DC marker CD83, up-regulation of the co-stimulatory molecules CD80 and CD86, up-regulation of MHC class I and MHC class II molecules, and down-regulation of the monocyte marker CD14. Also included was an analysis of the CD1a molecule that is supposed to be up-regulated on immature DCs, the common leukocyte marker CD45, and isotype controls. All markers showed the typically expected modulation except CD1a, which appears to be a feature of DCs cultivated in medium supplemented with human plasma instead of fetal calf serum (FIG. 1).

1.2. Mixed Leukocyte Reaction

Mature DCs were co-cultivated with allogeneic PBMCs in order to analyze the stimulatory capacity of DCs. It was shown consistently that DCs exposed to a LPS/IFN-γ maturation stimulus could trigger proliferation of allogeneic lymphocytes that was comparable when using the superantigens SEA and SEB as a proliferation stimulus (FIG. 2).

1.3. IL-12 Secretion

The supernatant of DC cultures 24 hours after exposure to the LPS/IFN-γ maturation stimulus was collected and the concentration of IL-12 p70 heterodimeric molecules was determined. The mean IL-12 concentration was 2.4±0.4 ng/$10^6$DCs/ml (FIG. 3). DCs that were maturated for 2 hours and re-cultured for 24 hours produced almost equal amounts of IL-12 p70 heterodimer as DCs that were maturated for 24 hours.

2. In Vitro Generation of Cytolytic Immunity

DCs were loaded with LCL-lysate derived soluble protein and used to stimulate autologous T-lymphocytes. The stimulation was repeated four times in weekly intervals. On the day of the stimulation the cell number was recorded and the percentage of HTLs and CTLs was determined. The cytolytic activity of the cultures was analyzed in a CTL assay on day 28. The stimulatory capacity of IL-12 secreting "active" DCs was compared with the stimulatory capacity of "exhausted" DCs that do not release IL-12 any more.

2.1. Antigen-Specific Expansion of T-Lymphocytes

Figure 4:
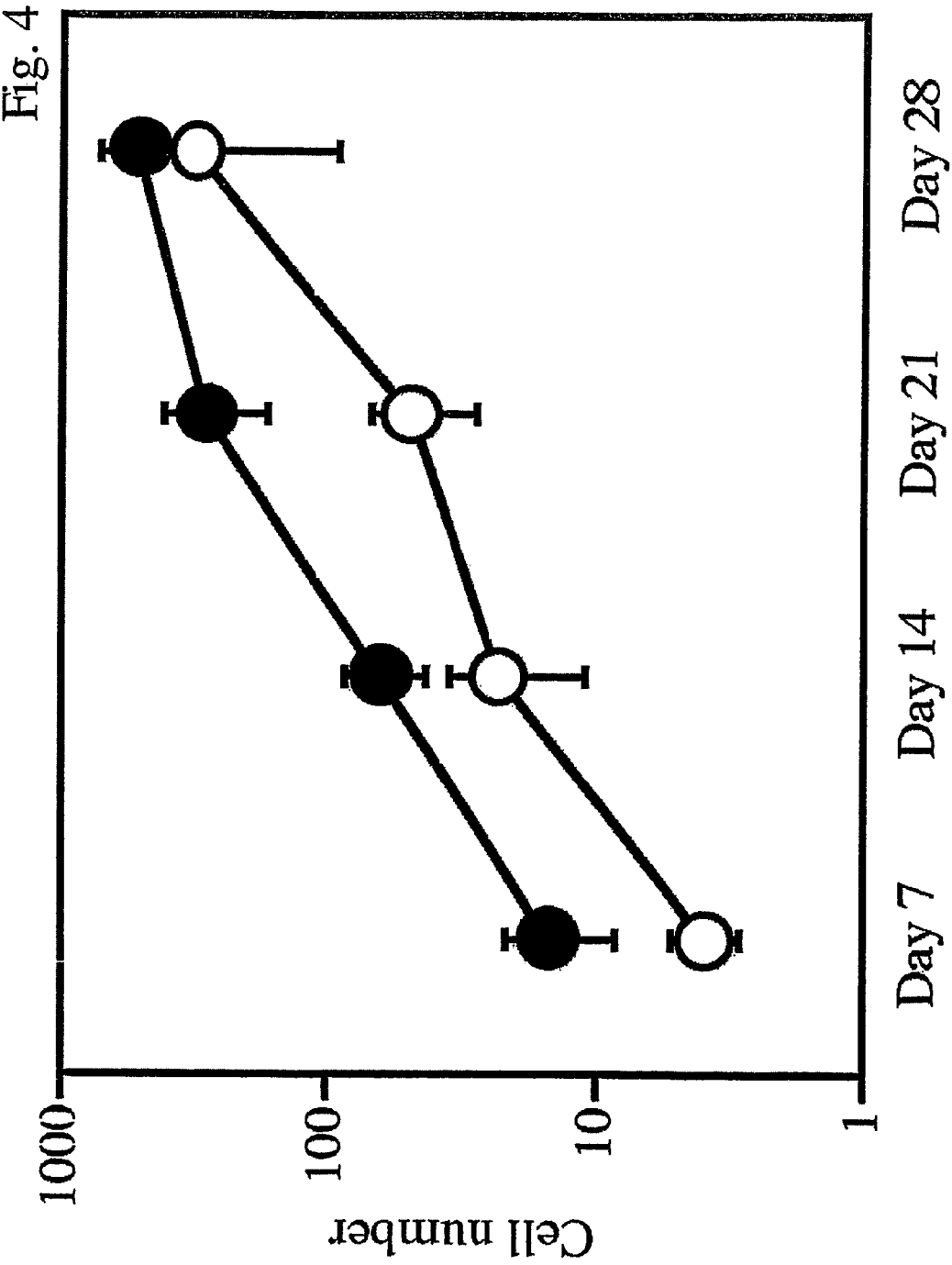

An approximately equal antigen-specific expansion of T-lymphocytes obtaining 531±198 million T-lymphocytes was observed when active DCs where used for stimulation and 318±228 million T-lymphocytes when using exhausted DCs for stimulation (FIG. 4). Also at the earlier time points no major differences in the growth kinetics of antigen-specific T-lymphocytes were observed even though T-lymphocytes exposed to active DCs tended to proliferate better compared to exposure to exhausted DCs.

2.2. Distribution of T-Lymphocyte Subpopulations during Antigen-Specific Expansion At each re-stimulation time point the subset distribution of CD3-positive T-lymphocytes was determined by immune phenotyping (FIG. 5). When using IL-12 secreting active DCs (n=10) a gradual decline in the percentage of CD4 positive HTLs (from 77±4% to 44±7%) was observed accompanied by a relative increase of CD8-positive CTLs (from 23±6% to 56±7%). In contrast, when exhausted DCs (n=10) were used for stimulation of T-lymphocytes, both the percentage of HTLs (79±4% on day 7 and 73±3% on day 28) and the percentage of CTLs (21±4 on day 7 and 27±3% on day 28) remained stable. This resulted in a significantly higher percentage of HTLs when comparing cultures that were stimulated with exhausted DCs with cultures that were stimulated with active DCs (p=0.0016 on day 28). The opposite effect was found by comparing the percentage of CTLs that was significantly higher after stimulation with active DCs as compared to stimulation with exhausted DCs (p=0.0016 on day 28).

2.3. Cytolytic Activity of T-Lymphocytes after Antigen-Specific Expansion

T-lymphocytes were exposed to LCL-lysate charged IL-12 secreting active DCs (n=3) or to exhausted DCs (n=5) that do not release IL-12. The cultures were re-stimulated weekly for four weeks and subjected to analysis of cytolytic activity on day 28. The specific lysis reached 55±9% after stimulation with active DCs compared to 12±5% after stimulation with exhausted DCs (p=0.0034) at the highest effector/target ratio of 25/1. The same tendency was evident at an effector/target ratio of 12.5/1 (27±7% vs. 7±2%, p=0.0125) and 6.25/1 (30±8% vs. 4±1%, p=0.0047).

3. Analysis of Murine Dendritic Cells

3.1. Immune Phenotype

Murine DCs were maturated with LPS/IFN-γ and the immune phenotype of immature and mature DCs was analyzed. MABs directed against CD11b, CD11c, MHC II, CD80, CD40, CD86 were used to characterize the maturation status of DCs. The typical CD11b/CD11c phenotype of mature DCs was consistently detected. Also up-regulation of the co-stimulatory molecules CD80 and CD86 was found as well as of CD40 and MHC II molecules.

3.2. IL-12 Secretion

The content of DC culture supernatant was analyzed for the presence of IL-12 one day after exposure to the LPS/IFN-γ maturation stimulus. DCs were washed 2 hours after LPS/IFN-γ stimulation and re-cultured for 24 hours in DC cultivation medium (active DCs) or left for 24 hours in medium without removing LPS and IFN-γ (exhausted DCs). In general about 2 ng/$10^6$ DCs/ml were detected (FIG. 8). DCs that were maturated for 2 hours produced almost equal amounts of IL-12 p70 heterodimer as DCs that were maturated for 24 hours.

4. Induction of Anti-Tumor Immunity in a Mouse Tumor Model

Having obtained suggestive evidence for the important role of IL-12 in the induction of a cytolytic immune response in vitro it was attempted to confirm these data in vivo. For that purpose a mouse tumor model was designed that allowed to immunize against a specific model antigen. The mouse tumor cell line K-Balb was engineered to express the bacterial protein NPT, which confers resistance to the neomycin analogue G418. Also recombinant NPT protein was produced in a bacterial expression system and affinity purified. Finally, an epitope prediction software was used to identify NPT-derived nonameric peptides with a high probability of binding to the antigen-presenting H-2b molecules of DCs from Balb/c mice.

Immature DCs were charged with the synthetic NPT-derived nonameric peptides, recombinant NPT protein, or soluble protein obtained from K-Balb-NPT cells by repeated freeze/thaw procedures. The loaded DCs were exposed to LPS/IFN-γ for 2 hours and injected into the animals in groups of 5 mice as IL-12 secreting active DCs, or maturated for 24 hours with LPS/IFN-γ, washed and injected as exhausted DCs that have lost their ability to release IL-12. In control groups mice were injected with irradiated K-Balb-NPT tumor cells, recombinant NPT protein, NPT-derived synthetic peptides, or with unloaded DCs. The immunized mice were challenged with NPT-transgenic K-Balb-NPT cells or with K-Balb wild type cells and the tumor growth was monitored (FIG. 9).

Independent of the immunization regime mice challenged with wild type K-Balb tumor cells developed progressively growing tumors. The same was true in the control groups with the exception of 1 mouse after immunization with unloaded DCs. Most importantly, in the groups of mice that were immunized with IL-12 secreting active DCs and challenged with K-Balb-NPT tumor cells, most of the mice were able to reject the tumor (3/5 immunized with K-Balb-NPT lysate loaded DCs, 5/5 immunized with DCs charged with recombinant NPT protein, 4/5 immunized with synthetic peptide loaded DCs). In contrast, almost all mice immunized with exhausted DCs were unable to reject K-Balb-NPT tumors (1/5 immunized with K-Balb-NPT lysate loaded DCs, 0/5 immunized with DCs charged with recombinant NPT protein, 1/5 immunized with synthetic peptide loaded DCs). All mice challenged with K-Balb wild type tumor cells developed progressively growing tumors providing evidence for an antigen-specific rejection response targeted at the NPT protein expressed by K-Balb-NPT tumor cells.

Phase I Trial to Demonstrate Feasibility and Lack of Toxicity of an IL-12-Secreting DC Immune Therapeutic Patients suffering from solid pediatric malignancies that had no more conventional treatment options were included in this trial.

The main objectives were to assess the feasibility and the toxicity of DC-ATIT. 20 patients enrolled in the study and 12 completed the treatment. The individual DC-ATIT immune therapeutics fulfilled all quality criteria including an immune phenotype typical for immature and mature DCs, respectively, release of 1 to 5 ng IL-12/$10^6$ DCs/ml, and a good stimulatory capacity in a mixed leukocyte reaction. The DC-ATIT immune therapeutic could be generated in sufficient quantity to complete the treatment schedule.

TABLE 1

Patients included into the clinical phase I DC-ATIT trial.

| Patient | Diagnosis | Age | Sex | Cycles |
|---|---|---|---|---|
| SH001 | Hepatocellular carcinoma | 15 | M | 3 |
| TM002 | Osteosarcoma | 21 | M | 3 |
| JS003 | Hepatocellular carcinoma | 10 | F | 1 |
| BG004 | Osteosarcoma | 17 | F | 1 |
| AE005 | Osteosarcoma | 8 | M | 3 |
| MR006 | Renal cell carcinoma | 7 | M | 3 |
| SiH007 | Ewing sarcoma | 22 | F | 3 |
| SA008 | Hepatocellular carcinoma | 13 | M | 2 |
| LS009 | Non-Hodgkin lymphoma | 14 | M | 0 |
| BT010 | Neuroblastoma | 20 | F | 0 |
| AR011 | Wilms tumor | 11 | F | 3 |
| JS012 | Renal cell carcinoma | 16 | F | 3 |
| SH(2)013 | Hepatocellular carcinoma | 15 | M | 3 |
| RC014 | Wilms tumor | 12 | F | 3 |
| JS(2)015 | Renal cell carcinoma | 16 | F | 3 |
| NH016 | Ewing sarcoma | 13 | F | 0 |
| TP017 | Ewing sarcoma | 22 | M | 0 |
| GK018 | Osteosarcoma | 15 | M | 0 |
| MK019 | Osteosarcoma | 10 | F | 3 |
| LS020 | Osteosarcoma | 13 | F | 3 |

The treatment was well tolerated and could be given in an outpatient setting. No major toxic side effects of the treatment were observed. Mild fever, most likely caused by an accompanying IFN-γ treatment that was applied with the intention of in situ up-regulation on of MHC class I molecule expression on tumor cells, could be controlled by antipyretics. Itching at the injection site of the DCs was treated locally with antihistaminics.

As an in vivo assay for the response to the DC-ATIT delayed type hypersensitivity testing was performed. Patients were injected intradermally with irradiated autologous tumor cells or the tracer antigen KLH as well as with a medium control and a negative control. All patients that completed the treatment showed a positive response to KLH. This provides convincing evidence that the DC-ATIT had the ability to trigger immunity. However, no anti-tumor immunity could be detected in these assays. The control injections did not result in any response.

All patients had advanced disease and had a history of extensive chemo- and radiotherapy as well as repeated surgeries. Hence, no objective tumor regression was observed in this trial. However, several of the patients had stable disease for a prolonged period of time.

DISCUSSION

Successful induction of IL-12 secretion by DCs appears to play a key role in generating a type 1 HTL response, which supports anti-tumor CTL activity [Cella, 1996]. In response to LPS, DCs produce IL-12 only transiently until about 18 to 20 hours after maturation [Langenkamp, 2000]. Hence, DCs taken at early time points after induction of maturation induce strong type 1 HTL polarization, whereas the same cells taken at late time points prime type 2 HTL polarized cells. These findings indicate a dynamic regulation of the generation of effector cell function.

It was observed that IL-12 secreting active DCs were able to equally trigger the expansion of CTLs and HTLs. In contrast, exhausted DCs that had lost the ability to release IL-12 caused the predominant expansion of HTLs. Consequently, T-lymphocytes primed by exposure to active DCs but not to exhausted DCs acquired the ability for antigen-specific lysis of target cells. Two model systems were used to demonstrate this. One was a human in vitro model that uses DCs charged with soluble protein from EBV-transformed LCLs for stimulation of autologous T-lymphocytes. Antigen-specific lysis of LCLs could be shown in this system. The second model was a murine tumor model. It was found that mice were protected from a tumor challenge after immunization with active but not with exhausted antigen-loaded DCs. Furthermore, a clinical phase I pilot trial was initiated to provide evidence for the feasibility and the lack of toxicity of IL-12 secreting DCs.

Cytolytic immune responses mediated by CTLs are dependent on antigen presentation via MHC class I molecules, which derive their antigenic peptides from cytoplasmic proteins, either from endogenously synthesized self-proteins or from non-self proteins during the course of an intracellular infection. Current paradigms hold that only professional antigen-presenting DCs can induce a primary immune response. Thus, DCs would have to take up non-self antigens from infected body cells in order to present them to CTLs, if they themselves are not infected and forced or enabled to synthesize these antigens endogenously. A large body of evidence, however, supports the concept that in DCs exogenously derived and sampled antigens are funneled primarily into the MHC class II antigen presentation pathway. To solve this apparent contradiction, the concept of cross-presentation was put forward. Supported by in vitro and in vivo evidence it implies the presentation of exogenously derived antigen in the MHC class I antigen presentation pathway by DCs. However, lately the importance of cross-presentation has been discussed controversially.

Recently, DCs charged ex vivo with tumor-associated or virus-derived antigens were used for therapeutic purposes in anti-tumor immune therapy or adoptive immune therapy for viral infections in immune compromised patients. In this context, cross-presentation is of central importance since frequently antigens are applied as soluble proteins. DCs exposed to these antigens will take them up by phagocytosis and without cross-presentation they would be processed exclusively in the MHC class II pathway and thus would not cause cytolytic immunity. The conditions that favor cross-presentation, however, are poorly defined and most evidence for the cross-presentation of exogenous antigens to CTLs that results in cytolytic anti-tumor or anti-viral immunity is indirect.

In anti-tumor and anti-viral immunity the role of CTLs received the most attention because most tumors or virus infected cells express MHC class I molecules but not MHC class II molecules. Moreover, CTLs are able to lyse cells directly upon recognition of peptide-MHC class I complexes, and their ability to eradicate large masses in vivo has been demonstrated. This preference has been bolstered by adoptive transfer studies in which CTL lines and clones specific for MHC class I restricted antigens that have been stimulated in vitro can mediate anti-tumor or antiviral immunity when transferred back into tumor-bearing hosts. Furthermore, recent reports suggest that immunization using tumor peptides loaded onto DCs can result in productive anti-tumor [Nestle, 2001] as well as anti-viral immunity [De-Bruijn, 1998].

One conclusion that is implied by the present invention is that active DCs at early time points after maturation with LPS/IFNγ fulfill the conditions for cross-presentation of exogenous antigens to CTLs. In contrast, exhausted DCs appear to have lost this ability. According to the present invention the release of IL-12 is used as a marker for active DCs [Langenkamp, 2000]. However, it is conceivable that the effect of IL-12 on CTLs is mediated by type 1 polarized HTLs that in turn support cross-presentation, CTL expansion, and cytolytic activity. A successful T-lymphocyte response against intracellular antigens such as virus-derived antigens or tumor-associated antigens is based on both CTLs and HTLs. However, HTLs have received less attention, which is remarkable given the pivotal role of these cells in regulating most antigen-specific immune responses. While it had long been imagined that HTL help for the development of CTLs occurs via the elaboration of lymphokines, more recent evidence has indicated that a critical pathway for delivery of help for CTLs, that is dependent on HTLs, uses the DC as an intermediary. In particular, interactions between CD40L and CD40 on the HTL and the DC appear critical in activating the DC to present antigens to, and co-stimulate the priming of, CTL precursors. In this scenario, the DCs represent the critical conduits between HTLs and CTLs that are specific for epitopes restricted by MHC class II and MHC class I, respectively. In this context the finding of an approximately equivalent amplification of HTLs and CTLs after stimulation with active but not with exhausted DCs seems to be of particular significance.

Due to the convincing evidence in both model systems used according to the present invention a clinical phase I pilot trial was initiated. Patients suffering from advanced solid malignancies of childhood were treated with active IL-12 releasing autologous DCs that were charged with soluble protein derived from the patient's tumor. Clinical trials using tumor antigen loaded DCs were conducted for different neoplastic diseases. However, the DCs used in these trials were either immature or matured with TNFα. Such DCs do not have the ability to release IL-12. Thus, in the light of the present preclinical experiments, these DCs have to be considered inferior to the IL-12 secreting DCs used in the present trial. All patients in the present study had advanced disease and had a history of extensive chemo- and radiotherapy. Hence, no objective tumor regression was observed in these patients. However, several of the patients had stable disease for a prolonged period of time. The toxicity of the treatment with our DC immune therapeutic was minimal.

In summary, it was found in a human in vitro model as well as a murine in vivo tumor model that IL-12-secreting active DCs early after maturation in contrast to exhausted DCs that have lost their ability to release IL-12 at later time points support the generation of cytolytic immune responses in vitro. Active DCs are enabled for cross-presentation of exogenous antigens on MHC class I molecules to CTLs whereas exhausted DCs do not have that ability. Expansion and cytolytic activity of CTLs is critically dependent on the presence of IL-12. The results provided with the present invention are of importance for the adoptive treatment of viral infections in immune compromised patients with ex vivo expanded antigen-specific T-lymphocytes. A clinical phase I pilot trial indicated the feasibility and the lack of toxicity of the treatment of neoplastic diseases with this DC immune therapeutic.

REFERENCES

Cella M et al., J. Exp Med 184:747, 1996
Hilkens C M et al., Blood 90:1920, 1997
Langenkamp A et al., Nat Immunol 1:3116, 2000
Nestle F O et al., Nat Med 7:7615, 2001
De-Bruijn M L et al., Cancer Res 58:724, 1998

The invention claimed is:

1. A method for the treatment of a tumor which comprises administering to a patient in need thereof an effective amount of active dendritic cells (DC) that are tumor-specific and secrete IL12, said tumor-specific and IL12-secreting DC being prepared by a process comprising:
    (a) collecting DC precursor cells from a suitable autologous or allogeneic source to obtain a DC culture;
    (b) loading the DC of said DC culture with a tumor specific antigen; and
    (c) exposing said DC culture to a concentration of LPS and a concentration of IFN-γ effective to trigger the DC of said DC culture to secrete IL12 to thereby obtain said tumor-specific and IL12-secreting DC, wherein said exposure to LPS and IFN-γ occurs over a period of 2-6 hours.

2. The method according to claim 1, wherein said treatment is performed after bone marrow transplantation.

3. The method according to claim 1, wherein said tumor is an advanced malignancy.

4. The method according to claim 1, wherein said DC are collected from the patient having said tumor or from a bone marrow donor.

5. The method according to claim 1, wherein the DCs have been loaded with an antigen from a tumor cell from said patient having said tumor.

6. The method according to claim 5, wherein the DC are additionally charged with a tracer antigen.

7. The method according to claim 6, wherein said tracer antigen is keyhole limpet hemocyanine (KLH).

8. The method according to claim 7, wherein the DCs are additionally charged with an adjuvant, especially with tetanus toxoid.

9. The method according to claim 1, wherein the active DC have been generated in vitro from peripheral blood mononuclear cells (PBMCs).

10. The method of claim 1 wherein said active DC are administered or frozen after exposure to LPS and IFN-γ.

11. The method of claim 1 wherein said exposure to LPS and IFN-γ occurs over a period of 2 hours.

12. The method of claim 1 wherein said exposure to LPS and IFN-γ occurs over a period of 6 hours.

13. A method for the treatment of a tumor which comprises administering to a patient in need thereof an effective amount of active dendritic cells (DC) that are tumor-specific and secrete IL12, said tumor-specific and IL12-secreting DC being prepared by a process consisting essentially of:
    (a) collecting DC precursor cells from a suitable autologous or allogeneic source to obtain a DC culture;
    (b) loading the DC of said DC culture with a tumor specific antigen; and
    (c) exposing said DC culture to a concentration of LPS and a concentration of IFN-γ effective to trigger the DC of said DC culture to secrete IL12 to thereby obtain said tumor-specific and IL12-secreting DC, wherein said exposure to LPS and IFN-γ occurs over a period of 2-6 hours.

14. A method for the treatment of a tumor consisting essentially of administering to a patient in need thereof an effective amount of active dendritic cells (DC), and wherein said active DC are prepared by a process consisting essentially of:
   (a) collecting DC precursor cells from a suitable autologous or allogeneic source to obtain a DC culture;
   (b) loading the DC of said DC culture with a tumor specific antigen; and
   (c) exposing said DC culture to a concentration of LPS and a concentration of IFN-γ effective to trigger the DC of said DC culture to secrete IL12 and thereby obtain said active DC, wherein said exposure to LPS and IFN-γ occurs over a period of 2-6 hours.

* * * * *